(12) United States Patent
Laskoski et al.

(10) Patent No.: US 9,920,165 B2
(45) Date of Patent: Mar. 20, 2018

(54) PHTHALONITRILES DERIVED FROM POLYPHENOLS

(71) Applicant: The Government of the United States of America, as Represented by the Secretary of the Navy, Washington, DC (US)

(72) Inventors: Matthew Laskoski, Springfield, VA (US); Teddy M. Keller, Fairfax Station, VA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/084,760

(22) Filed: Mar. 30, 2016

(65) Prior Publication Data

US 2016/0311976 A1 Oct. 27, 2016

Related U.S. Application Data

(60) Provisional application No. 62/151,466, filed on Apr. 23, 2015.

(51) Int. Cl.
*C08G 75/00* (2006.01)
*C08G 65/40* (2006.01)
(Continued)

(52) U.S. Cl.
CPC .............. *C08G 65/40* (2013.01); *C07C 37/66* (2013.01); *C07C 39/16* (2013.01); *C07C 39/17* (2013.01);
(Continued)

(58) Field of Classification Search
CPC ........ C08G 65/40; C08G 67/00; C08G 73/00; C08G 33/00
See application file for complete search history.

(56) References Cited

U.S. PATENT DOCUMENTS 4,587,325 A * 5/1986 Keller .................... C08G 73/00
252/500
8,841,405 B1 9/2014 Davis
(Continued)

OTHER PUBLICATIONS

Cash et al., "High Tg thermosetting resins from resveratrol" Polym. Chem., 2013, 4, 3859-3865 | 3859.
Hao et al., "Preparation of Hyperbranched Aromatic Polyimides via A2 + B3 Approach" Macromolecules 2002, 35, 5372-5381.
Long et al., "Preparation and characterization of poly(arylene ether nitrile)/copper phthalocyanine composites via sintering treatment" J. Mater. Sci.: Mater. Electron. (2014) 25:5505-5511.
(Continued)

*Primary Examiner* — Shane Fang
(74) *Attorney, Agent, or Firm* — US Naval Research Laboratory; Joseph T. Grunkemeyer

(57) ABSTRACT

A method of making an organic salt comprising: reacting a polyphenol with a base and optionally a dihaloaromatic compound. The polyphenol is resveratrol; dihydroresveratrol; 4,4'-(but-2-ene-1,4-diyl)bis-2-methoxyphenol; 4,4'-(1,4-butane-diyl)bis-2-methoxyphenol; 1-ethyl-2-methyl-3-(4-hydroxyphenyl)-5-hydroxyindane; 4,4'-(ethane-1,1-diyl) diphenol; 5,5'-methylenebis(2-methoxy-4-methylphenol); 4,4'-methylenebis(5-isopropyl-2-methylphenol); 4,4'-(1-ethyl-2-methyl-1,3-propanediyl)bisphenol; or 5,5'-(ethane-1,1-diyl)bis(2-methoxy-4-methylphenol). The dihaloaromatic compound if present comprises a carbonyl group, a sulfonyl group, a sulfinyl group, or a phosphoryl group. There is a molar excess of the hydroxy groups of the polyphenol relative to halo groups of the dihaloaromatic compound if present. The corresponding phthalonitrile monomers and thermosets made from the organic salts are disclosed.

24 Claims, 4 Drawing Sheets

Scheme 1

(51) Int. Cl.
*C08G 73/00* (2006.01)
*C07C 39/235* (2006.01)
*C07C 37/66* (2006.01)
*C07C 41/26* (2006.01)
*C07C 43/295* (2006.01)
*C07C 39/16* (2006.01)
*C07C 39/17* (2006.01)
*C07C 45/64* (2006.01)
*C07C 49/84* (2006.01)
*C08G 65/48* (2006.01)

(52) U.S. Cl.
CPC .......... *C07C 39/235* (2013.01); *C07C 41/26* (2013.01); *C07C 43/295* (2013.01); *C07C 45/64* (2013.01); *C07C 49/84* (2013.01); *C08G 65/48* (2013.01); *C08G 73/00* (2013.01)

(56) References Cited

U.S. PATENT DOCUMENTS 8,853,343 B1  10/2014  Davis et al.
8,927,685 B1   1/2015  Davis

OTHER PUBLICATIONS

Tong et al., "Crosslinking Behavior of Polyarylene Ether Nitrile Terminated with Phthalonitrile (PEN-t-Ph)/1,3,5-Tri-(3,4-dicyanophenoxy) Benzene (TPh) System and Its Enhanced Thermal Stability" J. Appl. Polym. Sci. 2013, DOI: 10.1002/APP.39312.
Yurtseven et al., "1. Synthesis, thermal, and electrical properties of stilbene-bridged polymeric zinc phthalocyanine" Designed Monomers and Polymers, vol. 17, Issue: 1, pp. 58-68 (Abstract), 2014.

* cited by examiner

Scheme 1

Scheme 2

PHTHALONITRILES DERIVED FROM POLYPHENOLS

This application claims the benefit of U.S. Provisional Application No. 62/151,466, filed on Apr. 23, 2015. The provisional application and all other publications and patent documents referred to throughout this nonprovisional application are incorporated herein by reference.

TECHNICAL FIELD

The present disclosure is generally related to phthalonitrile compounds.

DESCRIPTION OF RELATED ART

Phthalonitrile resins are showing potential as matrix materials for advanced composites for applications such as radomes, airframes, and electronics. The phthalonitrile monomers polymerize through the cyano groups, with the aid of an appropriate curing agent, to yield a crosslinked polymeric network with high thermal and oxidative stabilities. These polymers are obtained by heating the phthalonitrile monomers in the melt-state for extended periods of time at elevated temperatures in the presence of a small amount of curing additive. A variety of phthalonitrile monomers containing aromatic ether, thioether, imide, carbonyl, and sulfone linkages between the terminal phthalonitrile units have been synthesized and cured or converted to crosslinked/networked polymers. The cure reaction of these monomers have been investigated using a variety of curing additives such as organic amines, strong organic acids, strong organic acids/amine salts, metallic salts, and metals. When postcured at elevated temperatures at about 400° C., the thermoset shows excellent long-term thermal and oxidative stabilities to temperatures approaching 375° C. In addition, the high aromatic content of the thermoset affords a high char yield (>80%) when pyrolyzed to 1000° C. under inert conditions. The high thermal stability and the ability to form a high char yield upon pyrolysis contribute to the outstanding fire performance of the phthalonitrile polymer. For instance, the fire performance of phthalonitrile-carbon and phthalonitrile-glass composites are superior to that of other thermoset-based composites currently in use for aerospace, microelectronic, automotive, ship and submarine applications.

BRIEF SUMMARY

Disclosed herein is a method of making an organic salt comprising: reacting a polyphenol with a base and optionally in the presence of a dihaloaromatic compound. The polyphenol is resveratrol; dihydroresveratrol; 4,4'-(but-2-ene-1,4-diyl)bis-2-methoxyphenol; 4,4'-(1,4-butane-diyl)bis-2-methoxyphenol; 1-ethyl-2-methyl-3-(4-hydroxyphenyl)-5-hydroxyindane; 4,4'-(ethane-1,1-diyl)diphenol; 5,5'-methylenebis(2-methoxy-4-methylphenol); 4,4'-methylenebis(5-isopropyl-2-methylphenol); 4,4'-(1-ethyl-2-methyl-1,3-propanediyl)bisphenol; or 5,5'-(ethane-1,1-diyl)bis(2-methoxy-4-methylphenol). The dihaloaromatic compound if present comprises a carbonyl group, a sulfonyl group, a sulfinyl group, or a phosphoryl group. There is a molar excess of the hydroxy groups of the polyphenol relative to halo groups of the dihaloaromatic compound if present.

Also disclosed herein is a method comprising making a phthalonitrile mixture by mixing 1,3,5-tris(3,4-dicyanophenoxy)benzene with one of the compounds below; and curing the phthalonitrile mixture to form a thermoset. The value of n is a positive integer.

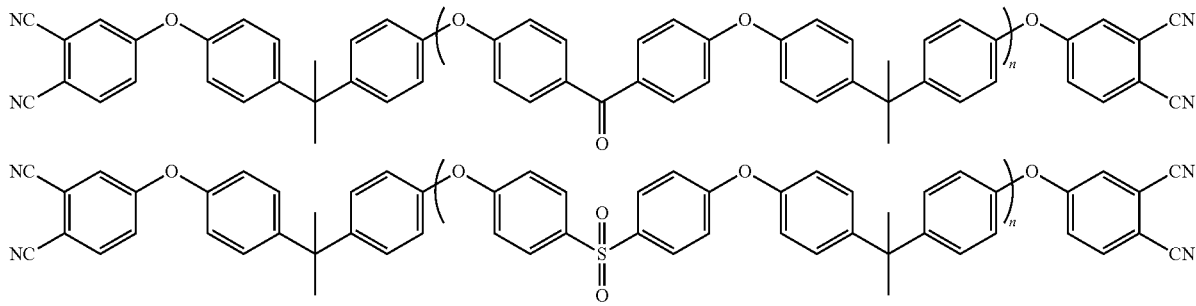

BRIEF DESCRIPTION OF THE DRAWINGS

A more complete appreciation will be readily obtained by reference to the following Description of the Example Embodiments and the accompanying drawings.

DETAILED DESCRIPTION OF EXAMPLE EMBODIMENTS

Figure 1:
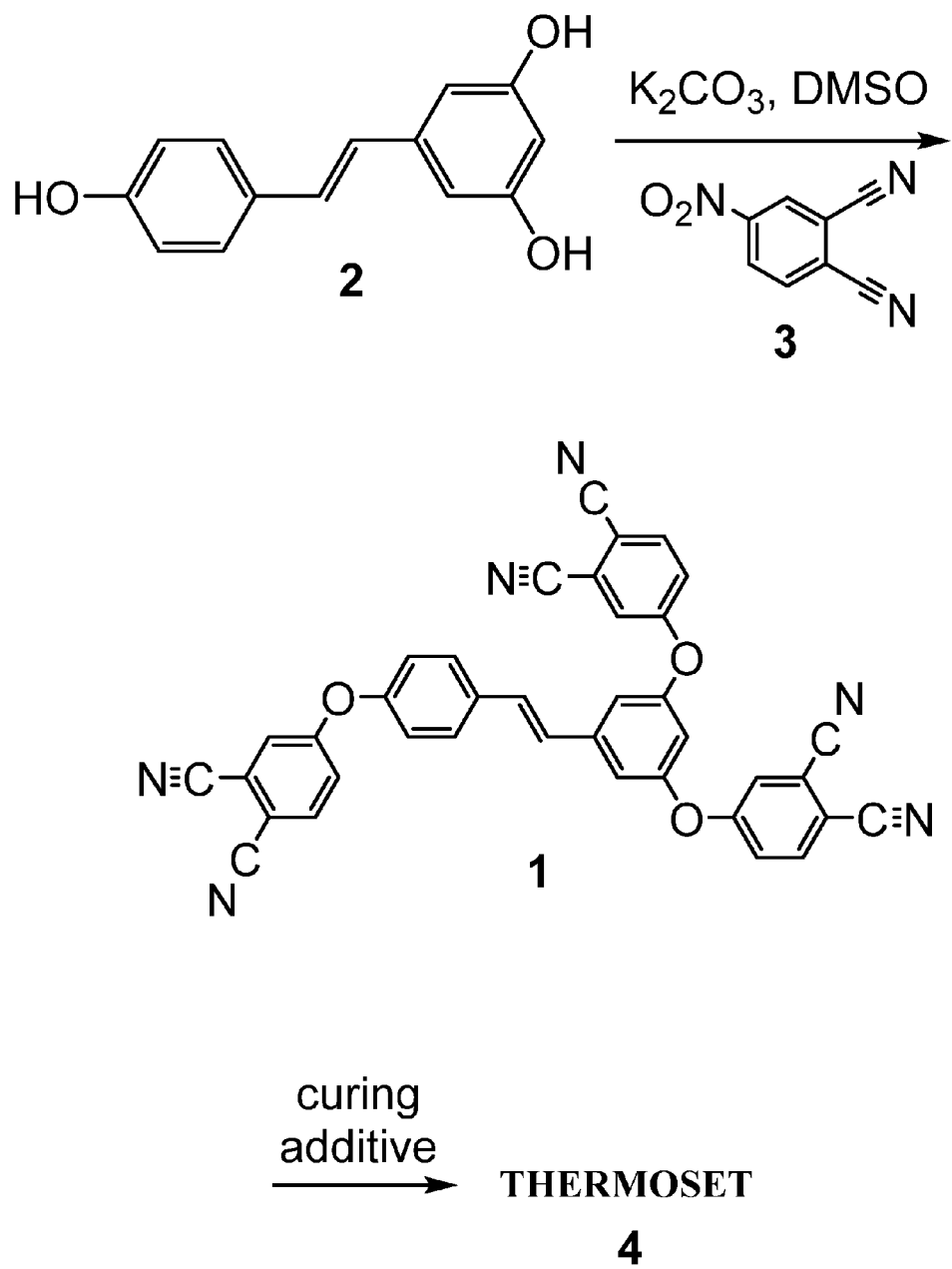
FIG. 1 shows Scheme 1—synthesis of simple phthalonitrile 1.

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed is the synthesis of certain low melting oligomeric phthalonitrile monomers containing multiple aromatic ether moieties and in some embodiments an alkenyl linkage between the terminal phthalonitrile units and their polymerization to thermoset phthalonitrile-based polymers. Additionally, the synthesis and polymerization of small molecule phthalonitrile monomers from multi-hydroxylated phenols is also disclosed. The phenols used for the synthesis of these phthalonitriles may be derived from renewable sources. Examples include resveratrol, extracted from grapes, and eugenol which is found in high concentrations in clove oil. The small molecule, oligomeric aromatic ether-alkenyl containing phthalonitrile monomers can polymerize through the phthalonitrile units to afford high temperature, flame resistant thermosets. Desirable physical properties such as the ability to control the glass transition temperature ($T_g$) and high thermal and oxidation stability can be obtained. Polymeric composites and coatings, formulated from these phthalonitriles, should have outstanding thermo-oxidative and flammability properties for ship, submarine, aerospace, microelectronic, automotive, and wind blade applications and can withstand continuous high temperatures (300-375° C.) in oxidative environments such as air for extended periods. To date, current oligomeric phthalonitrile polymers have melting points between 50 and 250° C. with the polymerization occurring in excess of 150° C. with fast reaction above 200° C. The use of low molecular weight precursor resins to obtain thermosetting polymeric materials with high thermo-oxidative properties is often advantageous from a processing standpoint. Precursor resins are useful in composite fabrication by a variety of methods such as infusion, resin transfer molding, filament winding, and prepreg consolidation. The phthalonitrile polymers/composites have potential for numerous aerospace, marine, electronic, and numerous domestic applications due to their outstanding and superior thermal and oxidative properties, ease of processability, and low water absorption relative to other high temperature polymers such as polyimides. Furthermore, resins with a large window between the melting point and the cure temperature are desirable to control the viscosity and controlled rate of curing to the thermoset. With the phthalonitrile monomers disclosed herein, processability to shaped composite components can be achieved in non-autoclave conditions potentially above 70° C. and by cost effective methods.

The phthalonitrile monomers incorporate units within the backbone to enhance the flammability resistance and thermo-oxidative properties while retaining low temperature processability. A low viscosity resin enables composite processing by resin transfer molding (RTM), resin infusion molding (RIM), filament winding, and other out-of-autoclave composite manufacturing methods. Furthermore, a low melt viscosity and a larger processing window are useful for fabrication of thick composite sections where the melt has to impregnate thick fiber preforms and the ability to control the exothermic polymerization reaction and reaction temperature is of importance. Low melting oligomeric phthalonitrile monomers and curing additives that do not volatilize at elevated cure reaction temperatures such as bis[4-(4-aminophenoxy)phenyl]sulfone (p-BAPS) or bis[4-(3-aminophenoxy)phenyl]sulfone (m-BAPS) have been shown to enhance the overall physical properties and processability of phthalonitrile-based composites. Since most high temperature resins are not amenable to low temperature oven cure due to initial high viscosities, high melting points, and the instability of the B-staged intermediate, the disclosed aliphatic containing phthalonitriles addresses the ease of processability into shaped void-free composite components by cost effective methods such as RTM and RTM.

Earlier simple bisphenol-based phthalonitriles had melting points in excess of 200° C. The synthesis of an amorphous phthalonitrile 1, which contains arylene ether and alkenyl (ethylene) units in the backbone and is derived from resveratrol 2, has been achieved by a one pot reaction involving a nucleophilic displacement reaction between the tripotassium salt of resveratrol 2 and 4-nitrophthalonitrile 3 in the presence of dimethylsulfoxide (DMSO) (FIG. 1, Scheme 1) at temperatures around 65° C. This afforded the simple phthalonitrile 1 in 98% yields, which was readily soluble in common organic solvents such as toluene, DMF, acetone, methylene chloride, ether, and chloroform. The structure of the phthalonitrile monomer 1 was confirmed by FTIR and $^1$H-NMR spectroscopy.

Figure 3:
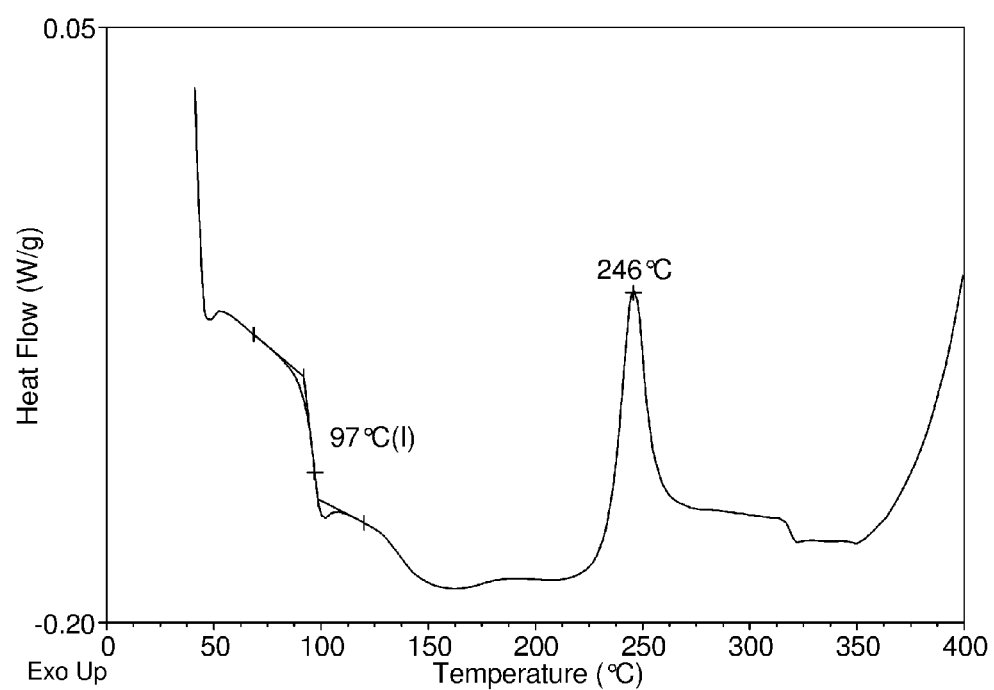
FIG. 3 shows DSC thermograms of phthalonitrile resin 1 cured with 3 mol % of p-BAPS.

Polymerization studies of phthalonitrile 1 were achieved by DSC analyses up to 400° C. in the presence of 3 weight % of bis[4-(4-aminophenoxy)phenyl]sulfone (p-BAPS) to afford thermoset 4. The DSC thermogram (FIG. 3) revealed an endothermic transition (glass transition temperature ($T_g$)) at approximately 95° C. and an exothermic transition peaking at about 225° C. and a further exotherm as seen above 350° C., both of which are attributed to the reaction with p-BAPS and propagation of the polymerization reaction.

Figure 2:
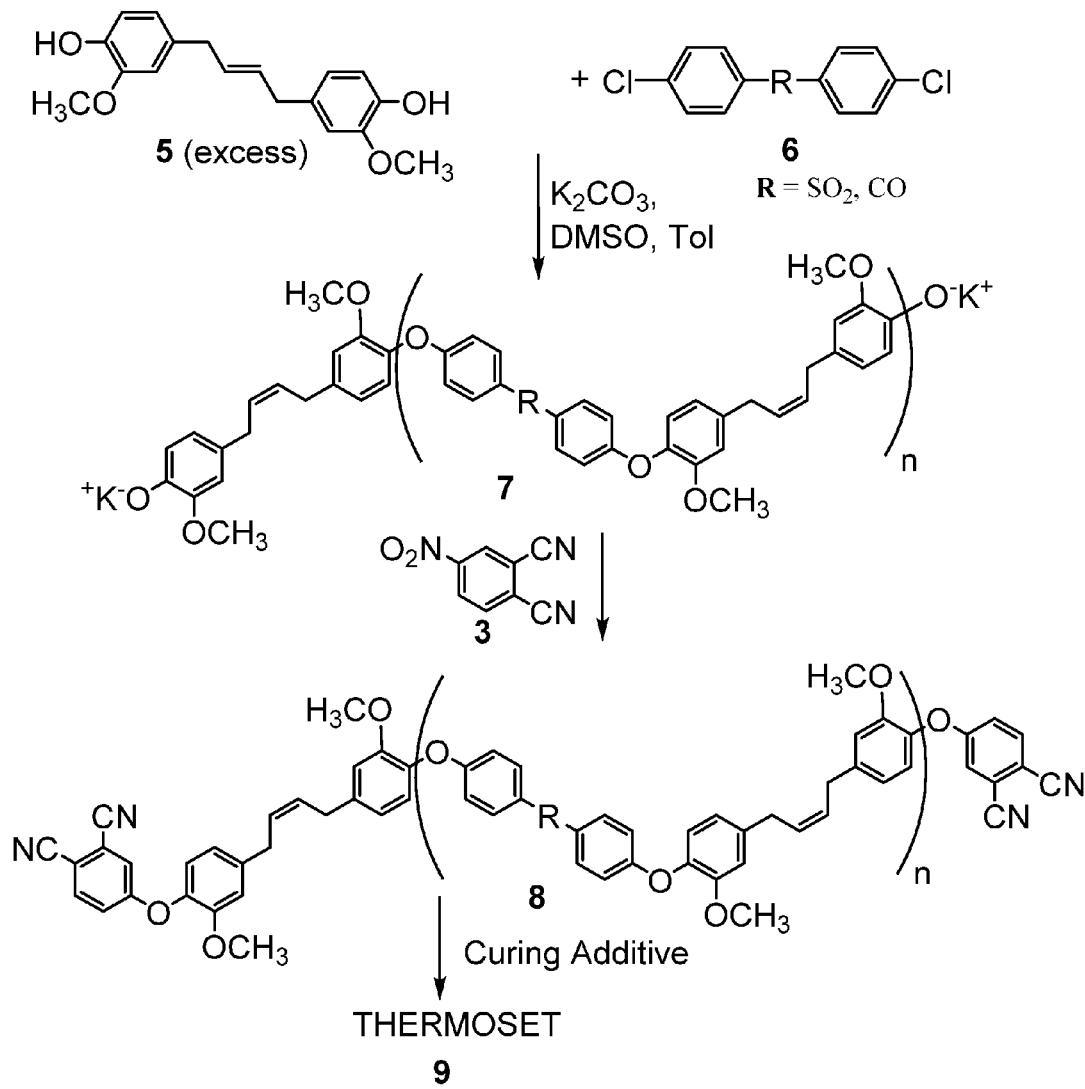
FIG. 2 shows Scheme 2—synthesis of oligomeric phthalonitrile 8.

Other low melting oligomeric phthalonitrile monomers were also prepared from renewable bisphenols, which upon polymerization would retain the useful thermal properties (300-375° C.) exhibited by the phthalonitrile polymers but with greater thermo-oxidative and superior flammability properties. Such monomers should exhibit a large processing window useful for composite and device fabrication. The "oligomeric" term means that more than one compound is formed during the synthesis of 8 (FIG. 2, Scheme 2) with the average molecular weight dependent on the ratios of reactants, 5 and 6, used, and can include some amount of 8 where n is 0. The synthesis of the multiple aromatic ether-linked phthalonitrile 8, which contains arylene ether and ethylene units in the backbone, has been achieved by a one pot reaction involving initially a nucleophilic displacement reaction between 4,4'-(but-2-ene-1,4-diyl)bis-2-methoxyphenol (derived from eugenol) 5, a dichloroaromatic compound 6, such as 4,4'-dichlorobenzophenone or 4-(chlorophenyl) sulfone, potassium carbonate, dimethylsulfoxide (DMSO) and toluene (Scheme 2) at temperatures around 150° C. Other activators may also work to enhance the displacement of the chloro unit, such as sulfinyl (—S(=O)—), phosphoryl (—P(=O)—), and multiple carbonyl or other units with the dichloroaromatic compound, to nucleophilic displacement. Other groups known in the art to be electron withdrawing groups may also be used. Once NMR spectroscopy confirmed the desired oligomeric diphenolate product 7, the displacement reaction was considered complete. Further reaction of 7 with 4-nitrophthalonitrile 3 afforded the oligomeric phthalonitrile 8 in 91-95% yields, which was readily soluble in common organic solvents such as toluene, DMF, acetone, methylene chloride, ether, and chloroform. The structure of the phthalonitrile monomer 8 was confirmed by FTIR and $^1$H-NMR spectroscopy. The length of the spacer between the terminal phthalonitrile groups can be varied by changing the ratio between 5 (excess) and 6. Oligomeric phthalonitrile resin 8 generally had a melting point between 50 and 70° C. Several oligomeric phthalonitriles can be synthesized by this method. Monomer 8 exhibited low softening temperatures and was completely free flowing above 100° C. as determined by a visual melting test and had a long processing window to ~150° C. before reaction with the curing additive started to occur. The polymerization studies on 8 showed similar DSC thermograms as for 1. The simple phthalonitrile derived from 5 can also be synthesized as monomer 1 prepared from resveratrol.

Figure 4:
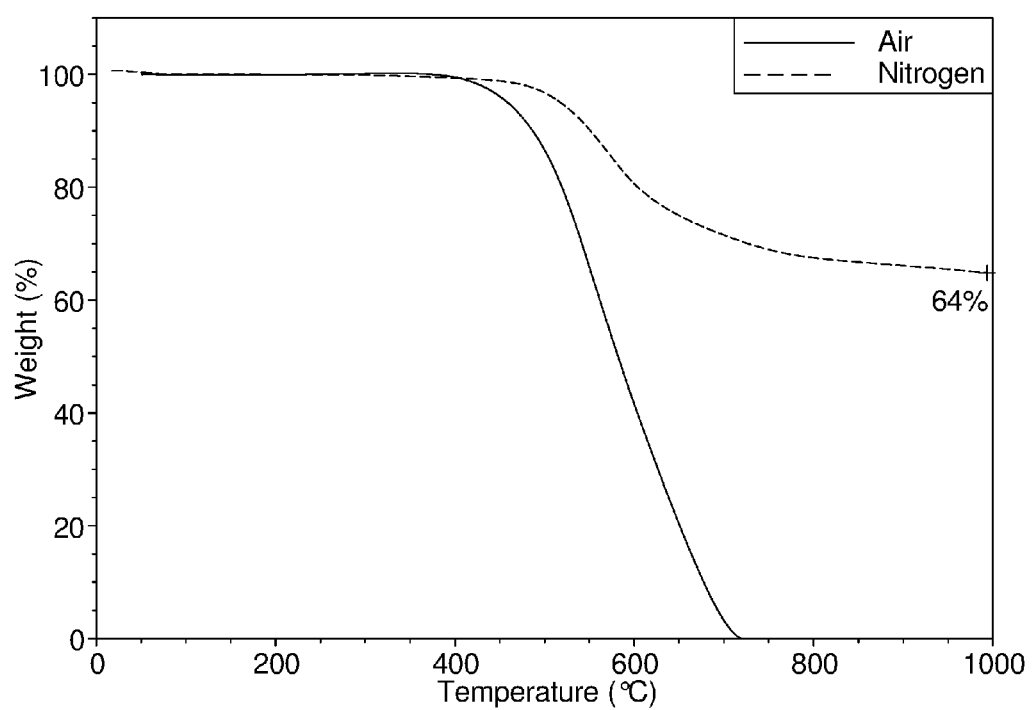
FIG. 4 shows TGA thermograms of a powdered resveratrol phthalonitrile resin 1 cured to 375° C. with 3 wt % p-BAPS heated under air and nitrogen atmospheres.

In the disclosed method, a renewable phenol 2 and low molecular weight diaryl ether-containing compounds 7 were used in the preparation of oligomeric phthalonitriles 1 and 8, respectively. The synthetic reaction to phthalonitriles 4 and 9 occurred below 100° C., which is much lower than previous highly aromatic phthalonitriles that had to be performed above 150° C. The phthalonitriles 1 and 8 were easily converted to polymers 4 and 9 under thermal conditions and in the presence of a curing additive. Under these curing conditions, the phthalonitrile monomers offer a broad processing window, which is important for the fabrication of complex shaped composite components. The thermosets or cured polymers show outstanding and superior thermo-oxidative properties. FIG. 4 shows TGA thermograms of the resveratrol derived phthalonitrile thermoset 4 containing an ethylene moiety between the phthalonitrile end groups that has been heated to 1000° C. The approach in using the renewable phenol 2 and other phenols such as 5 provides the ability to synthesize phthalonitrile resins with multiple aromatic ether linkages and also to vary the interconnecting alkenyl containing linkage to afford cured polymers with tailored physical properties. Moreover, for some applications, it might be desirable to advance the curing composition to a B-staged or prepolymer intermediate, which are stable indefinitely upon cooling to ambient conditions; this is a feature which is not available with other current thermosetting resins. In addition, due to the alkenyl-alkyl ether linkage of the phthalonitrile monomers 1 and 8, the stable glassy prepolymer intermediate or B-staged intermediate is readily soluble in common solvent for potential high temperature coating applications. When polymer 4 is used as a coating, it could be readily removed chemically by reaction and cleavage at the alkenyl units, if desired. In addition, the polymer 4 exhibits thermal and oxidative stability to about 400° C. before any significant weight loss occurred (FIG. 4). These resins should have relatively low viscosity values with the added feature of an optimal processing window for the molding of complex shapes using RTM or related composite processing methods. The phthalonitrile resins can also be readily blended or mixed with other phthalonitrile resins to affect desirable physical properties. Due to the superb thermal and oxidative stability of phthalonitrile polymers 4 and 9 cured to 400° C., the materials have potential for a variety of applications (ship, aerospace, marine, electronic, etc.) including its use in the fabrication of advanced composites by conventional prepreg consolidation, RTM, RIM, injection molding, and filament winding and as a coating for electronic devices. Thus, the phthalonitrile-based polymers from renewable phenols would be expected to exhibit improvements in specific physical properties when used at high temperatures or in a fire environment.

This is the first known reported synthesis of phthalonitrile 1 and conversion to thermosetting polymer 4 and the synthesis of oligomeric compound 7 followed by conversion to low melting oligomeric phthalonitriles 8 and polymerization to thermosetting polymer 9 with a large processing window between the melting point and the exothermic curing temperature. The phthalonitrile monomers 1 and 8, which display superb processability, can be readily cross-linked through the phthalonitrile groups yielding high temperature thermosetting polymers. The synthesis of a simple phthalonitrile 1, which contains aryl ether and ethylene units in the backbone and three phthalonitrile moieties, has been achieved by a nucleophilic displacement reaction utilizing a resveratrol 2 followed by end-capping with 4-nitrophthalonitrile 3 (Scheme 1). Likewise, the synthesis of a multiple aromatic ether-linked phthalonitrile 8, which contain an aryl ether and alkenyl units in the backbone, has been achieved by a nucleophilic displacement reaction utilizing a dichloroaromatic compound 6, such as 4,4'-dichlorobenzophenone and 4-(chlorophenyl) sulfone, and 4,4'-(but-2-ene-1,4-diyl) bis-2-methoxyphenol 5 (derived from eugenol) followed by end-capping with 4-nitrophthalonitrile 3 (Scheme 2). Other renewable phenols can be used in either synthesis.

All the reactions described herein may be performed by techniques known in the art, including but not limited to, those disclosed in U.S. Pat. No. 3,730,946, U.S. Pat. No. 3,763,210, U.S. Pat. No. 3,787,475, U.S. Pat. No. 3,869,499, U.S. Pat. No. 3,972,902, U.S. Pat. No. 4,209,458, U.S. Pat. No. 4,223,123, U.S. Pat. No. 4,226,801, U.S. Pat. No. 4,234,712, U.S. Pat. No. 4,238,601, U.S. Pat. No. 4,259,471, U.S. Pat. No. 4,304,896, U.S. Pat. No. 4,307,035, U.S. Pat. No. 4,315,093, U.S. Pat. No. 4,351,776, U.S. Pat. No. 4,408,035, U.S. Pat. No. 4,409,382, U.S. Pat. No. 4,410,676, U.S. Pat. No. 5,003,039, U.S. Pat. No. 5,003,078, U.S. Pat. No. 5,004,801, U.S. Pat. No. 5,132,396, U.S. Pat. No. 5,159,054, U.S. Pat. No. 5,202,414, U.S. Pat. No. 5,208,318, U.S. Pat. No. 5,237,045, U.S. Pat. No. 5,242,755, U.S. Pat. No. 5,247,060, U.S. Pat. No. 5,292,854, U.S. Pat. No. 5,304,625, U.S. Pat. No. 5,350,828, U.S. Pat. No. 5,352,760, U.S. Pat. No. 5,389,441, U.S. Pat. No. 5,464,926, U.S. Pat. No. 5,925,475, U.S. Pat. No. 5,965,268, U.S. Pat. No. 6,001,926, U.S. Pat. No. 6,297,298, U.S. Pat. No. 6,756,470, U.S. Pat. No. 6,891,014, U.S. Pat. No. 7,452,959, U.S. Pat. No. 7,511,113, U.S. Pat. No. 8,039,576, U.S. Pat. No. 8,222,403, U.S. Pat. No. 8,362,239, U.S. Pat. No. 8,530,607, U.S. Pat. No. 8,735,532, U.S. Pat. No. 8,859,712, U.S. Pat. No. 8,981,036, U.S. Pat. No. 8,921,510, and U.S. patent application Ser. No. 14/926,429.

In a first step for making the disclosed compounds, a polyphenol is reacted with a base and optionally a dihaloaromatic compound. Throughout this application, any description of a reactant may include one such reactant or a combination of more than one such reactant. The polyphenol may be any of those listed in Table 1.

TABLE 1

Polyphenols

| Compound | Structure |
|---|---|
| resveratrol (1-(4-hydroxyphenol)-4-(3,5-dihydroxyphenyl)-2-butene) | 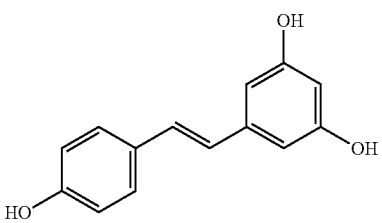 [SMILES: Oc1ccc(/C=C/c2cc(O)cc(O)c2)cc1] |

TABLE 1-continued

| Polyphenols | |
|---|---|
| Compound | Structure |
| dihydroresveratrol (1-(4-hydroxyphenol)-4-(3,5-dihydroxyphenyl)butane) | 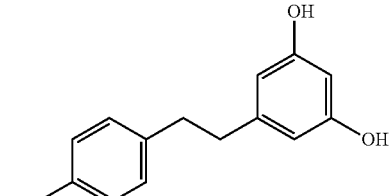 |
| 4,4'-(1,4-butane-diyl)bis-2-methoxyphenol | 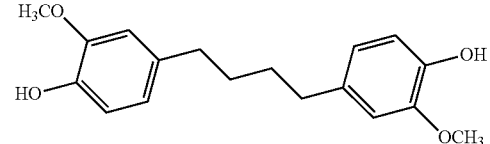 |
| 4,4'-(but-2-ene-1,4-diyl)bis-2-methoxyphenol | 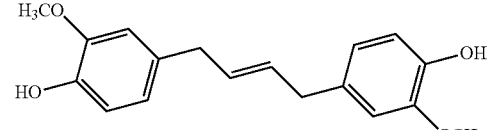 |
| 1-ethyl-2-methyl-3-(4-hydroxyphenyl)-5-hydroxyindane | 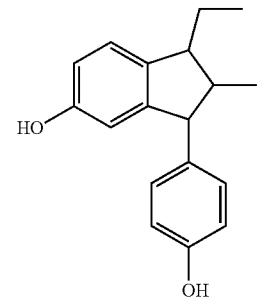 [SMILES: CCC1c2ccc(O)cc2C(c2ccc(O)cc2)C1C] |
| 4,4'-(1-ethyl-2-methyl-1,3-propanediyl)bisphenol | 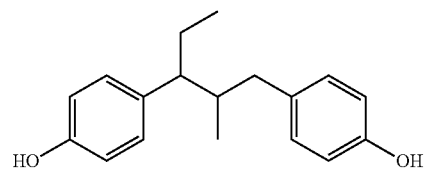 [SMILES: CCC(c1ccc(O)cc1)C(C)Cc1ccc(O)cc1] |
| 4,4'-(ethane-1,1-diyl)diphenol | 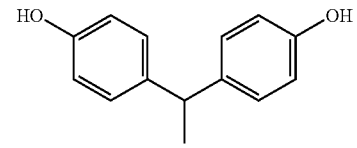 [SMILES: CC(c1ccc(O)cc1)c1ccc(O)cc1] |
| 5,5'-methylenebis(2-methoxy-4-methylphenol) | 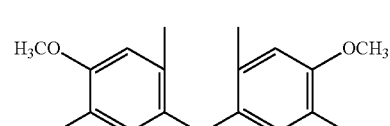 |
| 4,4'-methylenebis(5-isopropyl-2-methylphenol) | 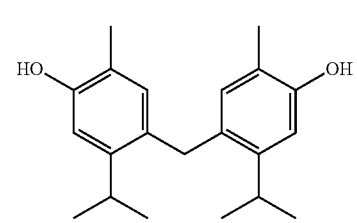 [SMILES: Cc1cc(Cc2cc(C)c(O)cc2C(C)C)c(C(C)C)cc1O] |

TABLE 1-continued

Polyphenols

| Compound | Structure |
|---|---|
| 5,5'-(ethane-1,1-diyl)bis(2-methoxy-4-methylphenol) | 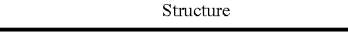 |

When the polyphenol is reacted with a base to make an organic salt, the hydroxyl groups are converted to $O^-M^+$, where $M^+$ is the cation of the base. Suitable bases include, but are not limited to, potassium carbonate and a combination of potassium carbonate and sodium hydroxide. If the dihaloaromatic compound is present, it comprises a carbonyl group, a sulfonyl group, a sulfinyl group, or a phosphoryl group. Suitable dihaloaromatic compounds include, but are not limited to, a dihalobenzophenone, 4,4'-dichlorobenzophenone, a dihalophenylsulfone, bis-4-(chlorophenyl)sulfone, a dihalophenylsulfoxide, or a dihalophenyl phosphine oxide. There should be a molar excess of the hydroxy groups of the polyphenol relative to halo groups of the dihaloaromatic compound so that the oligomer will terminate with the polyphenol. The ratio of the two will determine the average molecular weight of the oligomer. For example, a 3:2 molar ratio of hydroxyl groups to halo groups will result in an average value for n of 2 in the examples in Table 2. This is an average, so the product will contain a mixture of compounds having many values for n, including 0, as will the phthalonitrile monomers and thermosets made therefrom. Other ratios, such as 2:1, 4:3, and 21:20 may be used. Ratios between these adjacent integer ratios, such as for example 2.5:1, or excesses of 5, 10, 20, 30, or 40 mol %, will produce a significant amount of the polyphenol salt. The polyphenol salt will also react with 4-nitrophthalonitrile to form phthalonitrile monomers that can cure to a thermoset with or without longer phthalonitrile monomers. They may help to reduce the viscosity of the monomer blend before it cures, while still producing suitable properties in the thermoset. Suitable organic salt oligomers include, but are not limited to, those shown in Table 2.

TABLE 2

Oligomers

| Reactants | Oligomer |
|---|---|
| 4,4'-(but-2-ene-1,4-diyl)bis-2-methoxyphenol; 4,4'-dichlorobenzophenone | 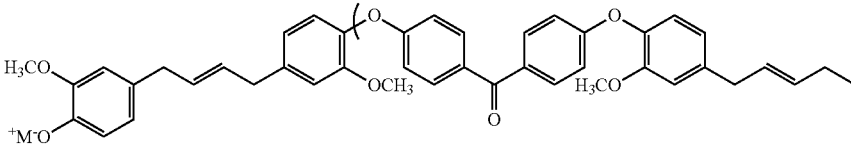 |
| 4,4'-(1,4-butane-diyl)bis-2-methoxyphenol; 4,4'-dichlorobenzophenone | 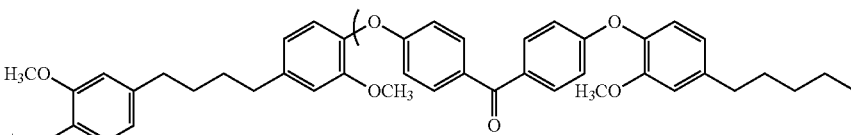 |
| 4,4'-(but-2-ene-1,4-diyl)bis-2-methoxyphenol; bis-4-(chlorophenyl)sulfone | 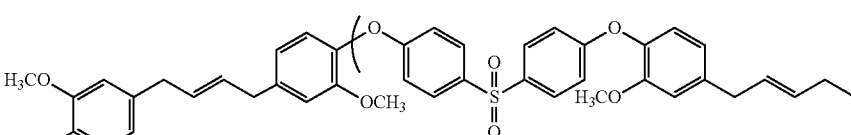 |
| 4,4'-(ethane-1,1-diyl)diphenol; 4,4'-dichlorobenzophenone | 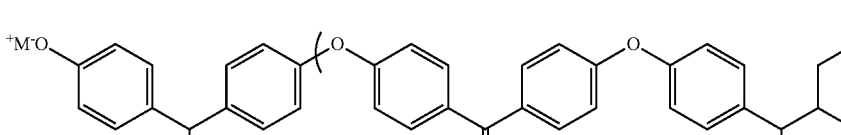 |

TABLE 2-continued

Oligomers

| Reactants | Oligomer |
|---|---|
| 5,5'-methylenebis(2-methoxy-4-methylphenol); 4,4'-dichlorobenzophenone | |
| 5,5'-(ethane-1,1-diyl)bis(2-methoxy-4-methylphenol; 4,4'-dichlorobenzophenone | |
| 4,4'-methylenebis(5-isopropyl-2-methylphenol); 4,4'-dichlorobenzophenone | |

In the next step the organic salt, whether an oligomer or small molecule, is reacted with 4-nitrophthalonitrile to form a phthalonitrile monomer. The reaction occurs at the oxygen anions as shown below.

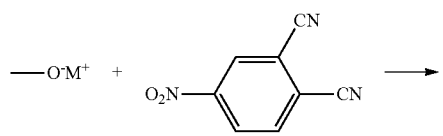

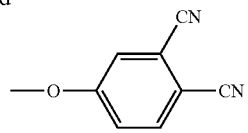

The phthalonitrile monomer may then be cured to a thermoset through the phthalonitrile groups. Thermoset formation may be by cyclization of the CN groups to form phthalocyanine groups, isoindoline groups, or triazine groups. Curing may be complete in one step or it may be performed in multiple stages as disclosed in U.S. Pat. No. 8,921,510. A curing agent may be used to promote the reaction, including but not limited to the curing agents listed in Table 3.

TABLE 3

Curing agents

| Name | Structure |
|---|---|
| bis[4-(4-aminophenoxy)phenyl]sulfone (p-BAPS) | 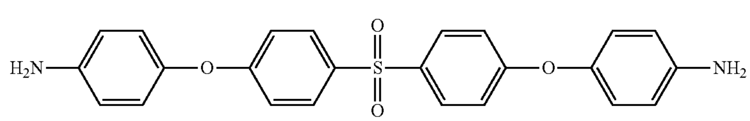 [SMILES: Nc1ccc(Oc2ccc(S(=O)(=O)c3ccc(Oc4ccc(N)cc4)cc3)cc2)cc1] |
| bis[4-(3-aminophenoxy)phenyl]sulfone (m-BAPS) | 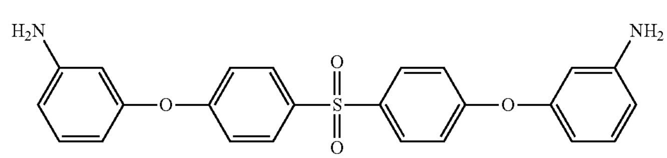 [SMILES: Nc1cccc(Oc2ccc(S(=O)(=O)c3ccc(Oc4cccc(N)c4)cc3)cc2)c1] |

TABLE 3-continued

Curing agents

| Name | Structure |
|---|---|
| 1,4-bis(3-aminophenoxy)benzene(p-APB) | H₂N–C₆H₄–O–C₆H₄–O–C₆H₄–NH₂ (3-aminophenoxy groups on 1,4-phenylene) |
| 1,3-bis(3-aminophenoxy)benzene(m-APB) | H₂N–C₆H₄–O–C₆H₄–O–C₆H₄–NH₂ (3-aminophenoxy groups on 1,3-phenylene) |

Before curing to a thermoset, the phthalonitrile monomer may be mixed or blended with other phthalonitriles to make a phthalonitrile mixture. The added phthalonitrile may be made from any of the polyphenols disclosed herein (Table 1) or oligomers thereof, such as those in Table 2. The added phthalonitrile may be a monophthalonitrile as disclosed in U.S. patent application Ser. No. 14/926,429, examples of which are shown in Table 4. Other options include 1,3,5-tris(3,4-dicyanophenoxy)benzene and oligomers made from bisphenol A and 4,4'-dichlorobenzophenone or bis-4-(chlorophenyl)sulfone, as shown in Table 5. In yet another embodiment, a thermoset is made by curing a mixture of 1,3,5-tris(3,4-dicyanophenoxy)benzene and an oligomer from Table 5 without the use of the other polyphenols disclosed herein.

TABLE 4

Monophthalonitriles

| Name | Structure |
|---|---|
| 4-dodecyl phthalonitrile | $C_{12}H_{25}$-substituted phthalonitrile |
| 4-(4-nonylphenoxy) phthalonitrile | $C_9H_{19}$–C₆H₄–O–phthalonitrile |

TABLE 4-continued

Monophthalonitriles

| Name | Structure |
|---|---|
| 4-(4-dodecylphenoxy) phthalonitrile | $C_{12}H_{25}$–C₆H₄–O–phthalonitrile |
| 4-(m-cumylphenoxy) phthalonitrile | NC-substituted phenyl–O–C₆H₄–C(CH₃)₂–C₆H₅ |
| 4-(3-hydroxyphenoxy)phthalonitrile | HO–C₆H₄–O–phthalonitrile |

TABLE 5

Other phthalonitriles

| Name | Structure |
|---|---|
| 1,3,5-tris(3,4-dicyano phenoxy)benzene | *(structure shown)* |
| bisphenol A/4,4'-dichlorobenzophenone oligomer | *(structure shown)* |
| bisphenol A/bis-4-(chlorophenyl)sulfone oligomer | *(structure shown)* |

The following examples are given to illustrate specific applications. These specific examples are not intended to limit the scope of the disclosure in this application.

Example 1

Synthesis of Resveratrol Phthalonitrile in One Reaction Pot

To a 1000 mL, three-necked flask fitted with a thermometer and a nitrogen inlet were added resveratrol (20.0 g, 87.6 mmol), 4-nitrophthalonitrile (47.0 g, 272 mmol), powdered anhydrous $K_2CO_3$ (50.0 g, 362 mol), and dimethylsulfoxide (DMSO) (1000 mL). The resulting mixture was degassed with nitrogen at ambient temperature and heated at 80° C. under a nitrogen atmosphere for 8-16 h. The mixture was allowed to cool to ambient temperature and poured into a 5% aqueous HCl solution resulting in the formation of a solid. The material was broken up and collected using a Büchner funnel. The white solid was washed with 200 mL of a 5% aqueous KOH solution, with 200 mL portions of distilled water until neutral, with 200 mL of a 5% aqueous HCl solution, and finally with 200 mL portions of water until neutral. The isolated solid was vacuum dried to yield the amorphous resveratrol phthalonitrile (52.4 g, 99% yield).

Example 2

Curing of a Resveratrol Phthalonitrile with an Aromatic Amine

Samples containing the resveratrol phthalonitrile from Example 1 and 2-5 weight % of either p-BAPS, m-BAPS, or m-APB were mixed by stirring at 200° C. for 2 minutes and cured by heating under nitrogen at 250° C. for 12 h (overnight) and at 375° C. for 8 h to afford a thermoset polymer. The polymers exhibited excellent thermal and oxidative stability up to 500° C. before any weight loss was detected. Catastrophic decomposition occurred after 600° C. in air.

Example 3

Synthesis of an Oligomeric Eugenol Phthalonitrile Based on 4,4'-(but-2-ene-1,4-diyl)bis-2-methoxyphenol (Derived from Eugenol) in One Reaction Pot To a 1000 mL, three-necked flask fitted with a thermometer and a nitrogen inlet were added 4,4'-(but-2-ene-1,4-diyl)bis-2-methoxyphenol (20.0 g, 63.2 mmol), 4-nitrophthalonitrile (23.0 g, 132 mmol), powdered anhydrous $K_2CO_3$ (26.0 g, 190 mol), and DMSO (1000 mL). The resulting mixture was degassed with nitrogen at ambient temperature and heated at 80° C. under a nitrogen atmosphere for 8-16 h. The mixture was allowed to cool to ambient temperature and poured into a 5% aqueous HCl solution resulting in the formation of a solid. The material was broken up and collected using a Büchner funnel. The white solid was washed with 200 mL of a 5% aqueous KOH solution, with 200 mL portions of distilled water until neutral, with 200 mL of a 5% aqueous HCl solution, and finally with 200 mL portions of water until neutral. The isolated solid was vacuum dried to yield the amorphous eugenol derived phthalonitrile (35.2 g, 98% yield).

Example 4

Curing of an Oligomeric Eugenol Phthalonitrile Based on 4,4'-(but-2-ene-1,4-diyl)bis-2-methoxyphenol with an Aromatic Amine Samples containing the eugenol derived phthalonitrile from Example 3 and 2-5 weight % of either p-BAPS, m-BAPS, or m-APB were mixed by stirring at 200° C. for 2 minutes and cured by heating under nitrogen at 250° C. for 12 h (overnight) and at 350° C. for 8 h to afford a thermoset polymer. The polymers exhibited excellent thermal and oxidative stability up to 400° C. before any weight loss was detected. Catastrophic decomposition occurred after 500° C. in air.

Example 5

Synthesis of 2:1 Oligomeric Hydroxyl Compound Based on 4,4'-(but-2-ene-1,4-diyl)bis-2-methoxyphenol and 4,4'-dichlorobenzophenone Isolated as the Potassium Salt To a 250 mL, three-necked flask fitted with a thermometer, a Dean-Stark trap with condenser, and a nitrogen inlet were added 4,4'-(but-2-ene-1,4-diyl)bis-2-methoxyphenol (15.0 g, 47.4 mmol), 4,4'-dichlorobenzophenone (5.95 g, 23.7 mmol), powdered anhydrous $K_2CO_3$ (14.4 g, 104 mmol), toluene (15 mL), and DMSO (100 mL). Toluene is used to control the refluxing azeotropic removal of water and to control the temperature of the reaction content. The resulting mixture was degassed with nitrogen at ambient temperature and the Dean-Stark trap was filled with toluene. The mixture was refluxed at 145-155° C. under a nitrogen atmosphere for 6-18 h or until no more water was observed being collected in the Dean-Stark trap. The toluene was then slowly distilled off causing the temperature to rise in the reaction vessel to enhance the yield of the intermediate hydroxyl salt and high conversion to this intermediate. The mixture was cooled and the dipotassium salt of the 2:1 oligomeric hydroxyl compound was left in solution to use in further reactions.

Example 6

Synthesis of 2:1 Oligomeric Phthalonitrile Based on 4,4'-(but-2-ene-1,4-diyl)bis-2-methoxyphenol and 4,4'-dichlorobenzophenone in One Reaction Pot To a 250 mL, three-necked flask fitted with a thermometer, a Dean-Stark trap with condenser, and a nitrogen inlet were added 4,4'-(but-2-ene-1,4-diyl)bis-2-methoxyphenol (15.0 g, 47.4 mmol), 4,4'-dichlorobenzophenone (5.95 g, 23.7 mmol), powdered anhydrous $K_2CO_3$ (14.4 g, 104 mmol), toluene (15 mL), and DMSO (100 mL). Toluene is used to control the refluxing azeotropic removal of water and to control the temperature of the reaction content. The resulting mixture was degassed with nitrogen at ambient temperature and the Dean-Stark trap was filled with toluene. The mixture was refluxed at 145-155° C. under a nitrogen atmosphere for 6-18 h or until no more water was observed being collected in the Dean-Stark trap. The toluene was then slowly distilled and the mixture was cooled to 50° C. At this time, 4-nitrophthalonitrile (8.96 g, 51.9 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was washed with 200 mL of a 5% aqueous KOH solution, with 200 mL portions of distilled water until neutral, with 200 mL of a 5% aqueous HCl solution, and finally with 200 mL portions of water until neutral. The isolated solid was vacuum dried to yield the 2:1 oligomeric phthalonitrile (24.7 g, 97% yield).

Example 7

Curing of an Oligomeric Eugenol Phthalonitrile Based on 4,4'-(but-2-ene-1,4-diyl)bis-2-methoxyphenol and 4,4'-dichlorobenzophenone with an Aromatic Amine Samples containing the 2:1 oligomeric phthalonitrile from Example 6 and 2-5 weight % of either p-BAPS, m-BAPS, or m-APB were mixed by stirring at 200° C. for 2 minutes and cured by heating under nitrogen at 250° C. for 12 h (overnight) and at 350° C. for 8 h to afford a thermoset polymer. The polymers exhibited excellent thermal and oxidative stability up to 400° C. before any weight loss was detected. Catastrophic decomposition occurred after 500° C. in air.

Example 8

Synthesis of 2:1 Oligomeric Hydroxyl Compound Based on 4,4'-(but-2-ene-1,4-diyl)bis-2-methoxyphenol and 4,4'-dichlorophenylsulfone Isolated as the Potassium Salt To a 250 mL, three-necked flask fitted with a thermometer, a Dean-Stark trap with condenser, and a nitrogen inlet were added 4,4'-(but-2-ene-1,4-diyl)bis-2-methoxyphenol (15.0 g, 47.4 mmol), 4,4'-dichlorophenylsulfone (6.81 g, 23.7 mmol), powdered anhydrous $K_2CO_3$ (14.4 g, 104 mmol), toluene (15 mL), and DMSO (100 mL). Toluene is used to control the refluxing azeotropic removal of water and to control the temperature of the reaction content. The resulting mixture was degassed with nitrogen at ambient temperature and the Dean-Stark trap was filled with toluene. The mixture was refluxed at 145-155° C. under a nitrogen atmosphere for 6-18 h or until no more water was observed being collected in the Dean-Stark trap. The toluene was then slowly distilled off causing the temperature to rise in the reaction vessel to enhance the yield of the intermediate hydroxyl salt and high conversion to this intermediate. The mixture was cooled and the dipotassium salt of the 2:1 oligomeric hydroxyl compound was left in solution to use in further reactions.

Example 9

Synthesis of 2:1 Oligomeric Phthalonitrile Based on 4,4'-(but-2-ene-1,4-diyl)bis-2-methoxyphenol and 4,4'-dichlorophenylsulfone in One Reaction Pot To a 250 mL, three-necked flask fitted with a thermometer, a Dean-Stark trap with condenser, and a nitrogen inlet were added 4,4'-(but-2-ene-1,4-diyl)bis-2-methoxyphenol (15.0 g, 47.4 mmol), 4,4'-dichlorophenylsulfone (6.81 g, 23.7 mmol), powdered anhydrous $K_2CO_3$ (14.4 g, 104 mmol), toluene (15 mL), and DMSO (100 mL). Toluene is used to control the refluxing azeotropic removal of water and to control the temperature of the reaction content. The resulting mixture was degassed with nitrogen at ambient temperature and the Dean-Stark trap was filled with toluene. The mixture was refluxed at 145-155° C. under a nitrogen atmosphere for 6-18 h or until no more water was observed being collected in the Dean-Stark trap. The toluene was then slowly distilled and the mixture was cooled to 50° C. At this time, 4-nitrophthalonitrile (8.95 g, 51.7 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was washed with 200 mL of a 5% aqueous KOH solution, with 200 mL portions of distilled water until neutral, with 200 mL of a 5% aqueous HCl solution, and finally with 200 mL portions of water until neutral. The isolated solid was vacuum dried to yield the 2:1 oligomeric phthalonitrile (25.2 g, 96% yield).

Example 10

Curing of an Oligomeric Eugenol Phthalonitrile Based on 4,4'-(but-2-ene-1,4-diyl)bis-2-methoxyphenol and 4,4'-dichlorophenylsulfone with an Aromatic Amine Samples containing the 2:1 oligomeric phthalonitrile from Example 9 and 2-5 weight % of either p-BAPS, m-BAPS, or m-APB were mixed by stirring at 200° C. for 2 minutes and cured by heating under nitrogen at 250° C. for 12 h (overnight) and at 350° C. for 8 h to afford a thermoset polymer. The polymers exhibited excellent thermal and oxidative stability up to 400° C. before any weight loss was detected. Catastrophic decomposition occurred after 500° C. in air.

Example 11

Mixture of an Oligomeric Eugenol Phthalonitrile Based on 4,4'-(but-2-ene-1,4-diyl)bis-2-methoxyphenol and 4,4'-dichlorophenylsulfone with the Resveratrol Phthalonitrile Cured with an Aromatic Amine The 2:1 oligomeric phthalonitrile (1 g) from Example 9 and the resveratrol phthalonitrile (300 mg) from Example 1 were melted and mixed thoroughly using a stirring rod for 2 min at 200° C. in an aluminum pan. Next, 2-5 weight % of either p-BAPS, m-BAPS, or m-APB was added and stirred at 200° C. for 2 minutes. The resulting mixture was cured under by heating under nitrogen at 250° C. for 12 h (overnight) and at 350° C. for 8 h to afford a thermoset polymer. The polymers exhibited excellent thermal and oxidative stability, due to the increased crosslinking density imparted by the resveratrol phthalonitrile, up to 450° C. before any weight loss was detected. Catastrophic decomposition occurred after 500° C. in air.

Example 12

Mixture of an Oligomeric Eugenol Phthalonitrile Based on 4,4'-(but-2-ene-1,4-diyl)bis-2-methoxyphenol and 4,4'-dichlorobenzophenone with a Resveratrol Phthalonitrile Cured with an Aromatic Amine The 2:1 oligomeric phthalonitrile (2 g) from Example 6 and the resveratrol phthalonitrile (1 g) from Example 1 were melted and mixed thoroughly using a stirring rod for 2 min. at 200° C. in an aluminum pan. Next, 2-5 weight % of either p-BAPS, m-BAPS, or m-APB was added and stirred at 200° C. for 2 minutes. The resulting mixture was cured by heating under nitrogen at 250° C. for 12 h (overnight) and at 350° C. for 8 h to afford a thermoset polymer. The polymers exhibited excellent thermal and oxidative stability, due to the increased crosslinking density imparted by the resveratrol phthalonitrile, up to 450° C. before any weight loss was detected. Catastrophic decomposition occurred after 500° C. in air.

Example 13

Synthesis of Phthalonitrile Based on 1,3,5-trihydroxybenzene in One Reaction Pot To a 1000 mL, three-necked flask fitted with a thermometer and a nitrogen inlet were added 1,3,5-trihydroxybenzene (20.0 g, 159 mmol), 4-nitrophthalonitrile (85.1 g, 492 mmol), powdered anhydrous $K_2CO_3$ (87.5 g, 634 mol), and DMSO (1000 mL). The resulting mixture was degassed with nitrogen at ambient temperature and heated at 80° C. under a nitrogen atmosphere for 8-16 h. The mixture was allowed to cool to ambient temperature and poured into a 5% aqueous HCl solution resulting in the formation of a solid. The material was broken up and collected using a Büchner funnel. The white solid was washed with 200 mL of a 5% aqueous KOH solution, with 200 mL portions of distilled water until neutral, with 200 mL of a 5% aqueous HCl solution, and finally with 200 mL portions of water until neutral. The isolated solid was vacuum dried to yield the phthalonitrile based on 1,3,5-trihydroxybenzene (73.3 g, 92% yield) as a tan solid with a melting point of 268° C.

Example 14

Mixture of an Oligomeric Eugenol Phthalonitrile Based on 4,4'-(but-2-ene-1,4-diyl)bis-2-methoxyphenol and 4,4'-dichlorobenzophenone with a Phthalonitrile Based on 1,3,5-trihydroxybenzene Cured with an Aromatic Amine The 2:1 oligomeric phthalonitrile (2 g) from Example 6 and the phthalonitrile (600 mg) based on 1,3,5-trihydroxybenzene from Example 13 were melted and mixed thoroughly using a stirring rod for 2 min. at 200° C. in an aluminum pan. Next, 2-5 weight % of either p-BAPS, m-BAPS, or m-APB was added and stirred at 200° C. for 2 minutes. The resulting mixture was cured by heating under nitrogen at 250° C. for 12 h (overnight) and at 350° C. for 8 h to afford a thermoset polymer. The polymers exhibited excellent thermal and oxidative stability, due to the increased crosslinking density imparted by the phthalonitrile based on 1,3,5-trihydroxybenzene, up to 450° C. before any weight loss was detected. Catastrophic decomposition occurred after 500° C. in air.

Example 15

Synthesis of 2:1 Oligomeric Phthalonitrile Based on Bisphenol A (30% Excess) and bis(4-chlorophenyl)sulfone in One Reaction Pot Using NaOH To a 500 mL, three-necked flask fitted with a thermometer, a Dean-Stark trap with condenser, and a nitrogen inlet were added bisphenol A (50 g, 219 mmol), bis(4-chlorophenyl)sulfone (22.0 g, 76.7 mmol), sodium hydroxide (20.0 g, 500 mmol), toluene (50 mL), and DMSO (250 mL). Toluene is used to control the refluxing azeotropic removal of water and to control the temperature of the reaction content. The resulting mixture was degassed with nitrogen at ambient temperature and the Dean-Stark trap was filled with toluene. The mixture was refluxed at 145-155° C. under a nitrogen atmosphere for 8-16 h or until no more water was observed being collected in the Dean-Stark trap. The toluene was then slowly distilled off causing the temperature to rise in the reaction vessel to enhance the yield of the intermediate hydroxyl salt and high conversion to this intermediate. The mixture was cooled to 50° C. At this time, 4-nitrophthalonitrile (50.6 g, 292 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was washed with 200 mL of a 5% aqueous KOH solution, with 200 mL portions of distilled water until neutral, with 200 mL of a 5% aqueous HCl solution, and finally with 200 mL portions of water until neutral. The isolated solid was vacuum dried to yield the 2:1 oligomeric phthalonitrile (100 g, 98% yield).

Example 16

Mixture of a 2:1 Oligomeric Phthalonitrile Based on Bisphenol a (30% Excess) and bis(4-chlorophenyl)sulfone with a Phthalonitrile Based on 1,3,5-trihydroxybenzene Cured with an Aromatic Amine The 2:1 oligomeric phthalonitrile (1 g) from Example 15 and the phthalonitrile (300 mg) based on 1,3,5-trihydroxybenzene from Example 13 were melted and mixed thoroughly using a stirring rod for 2 min. at 200° C. in an aluminum pan. Next, 2-5 weight % of either p-BAPS, m-BAPS, or m-APB was added and stirred at 200° C. for 2 minutes. The mixture was cured by heating under nitrogen at 250° C. for 12 h (overnight) and at 350° C. for 8 h to afford a thermoset polymer. The polymers exhibited excellent thermal and oxidative stability, due to the increased crosslinking density imparted by the phthalonitrile based on 1,3,5-trihydroxybenzene, up to 500° C. before any weight loss was detected. Catastrophic decomposition occurred after 600° C. in air.

Example 17

Synthesis of 2:1 Oligomeric Phthalonitrile Based on Bisphenol A (30% Excess) and 4,4'-dichlorobenzophenone in One Reaction Pot To a 2000 mL, three-necked flask fitted with a thermometer, a Dean-Stark trap with condenser, and a nitrogen inlet were added bisphenol A (100 g, 438 mmol), 4,4'-dichlorobenzophenone (38.5 g, 153 mmol), powdered anhydrous $K_2CO_3$ (90.0 g, 632 mmol), toluene (25 mL), and DMSO (500 mL). Toluene is used to control the refluxing azeotropic removal of water and to control the temperature of the reaction content. The resulting mixture was degassed with nitrogen at ambient temperature and the Dean-Stark trap was filled with toluene. The mixture was refluxed at 135-145° C. under a nitrogen atmosphere for 6 h or until no more water was observed being collected in the Dean-Stark trap. The toluene was then slowly distilled off causing the temperature to rise in the reaction vessel to enhance the yield of the intermediate hydroxyl salt and high conversion to this intermediate. The reaction mixture was heated above 180° C. for an additional 12 h with a very small amount of toluene present to control the temperature, to totally remove the water, formed as a by-product, so that the reaction can be pushed to completion and high conversion to the hydroxyl salt intermediate. The mixture was cooled to 50° C. At this time, 4-nitrophthalonitrile (99.1 g, 573 mmol) was added in one portion and the reaction mixture was heated at 80° C. for 6-8 h. The mixture was allowed to cool to ambient temperature and poured into a 5% aqueous HCl solution resulting in the formation of a solid. The material was broken up and collected using a Büchner funnel. The white solid was washed with 200 mL of a 5% aqueous KOH solution, with 200 mL portions of distilled water until neutral, with 200 mL of a 5% aqueous HCl solution, and finally with 200 mL portions of water until neutral. The isolated solid was vacuum dried to yield the 2:1 oligomeric phthalonitrile (192 g, 97% yield). IR [cm$^{-1}$]: ν 3077 (C=CH), 2232 (CN), 1586 (C=C), 1478 (aromatic), 1306 (aromatic), 1308 (C—O), 1245 (CH$_3$), 1162 (C—O), 929 (C—O), 847 (aromatic).

Example 18

Mixture of the 2:1 Oligomeric Phthalonitrile Based on Bisphenol A (30% Excess) and 4,4'-dichlorobenzophenone with a Resveratrol Phthalonitrile Cured with an Aromatic Amine The 2:1 oligomeric phthalonitrile (2 g) from Example 17 and the resveratrol phthalonitrile (1 g) from Example 1 were melted at 200° C. in an aluminum pan and mixed thoroughly using a stirring rod for 2 min. Next, 2-5 weight % of either p-BAPS, m-BAPS, or m-APB was added and stirred at 200° C. for 2 minutes. The mixture was cured by heating under nitrogen at 250° C. for 12 h (overnight) and at 350° C. for 8 h to afford a thermoset polymer. The polymers exhibited excellent thermal and oxidative stability, due to the increased crosslinking density imparted by the resveratrol phthalonitrile, up to 500° C. before any weight loss was detected. Catastrophic decomposition occurred after 600° C. in air.

Example 19

Synthesis of Dihydroresveratrol Phthalonitrile in One Reaction Pot

To a 1000 mL, three-necked flask fitted with a thermometer and a nitrogen inlet were added dihydroresveratrol (15.0 g, 65.1 mmol), 4-nitrophthalonitrile (35.0 g, 201 mmol), powdered anhydrous $K_2CO_3$ (27.9 g, 202 mmol), and DMSO (300 mL). The resulting mixture was degassed with nitrogen at ambient temperature and heated at 80° C. under a nitrogen atmosphere for 8-16 h. The mixture was allowed to cool to ambient temperature and poured into a 5% aqueous HCl solution resulting in the formation of a solid. The material was broken up and collected using a Büchner funnel. The white solid was washed with 200 mL of a 5% aqueous HCl solution, and finally with 200 mL portions of water until neutral. The isolated solid was vacuum dried to yield the amorphous dihydroresveratrol phthalonitrile (38.6 g, 97%).

Example 20

Curing of a Dihydroresveratrol Phthalonitrile with an Aromatic Amine

Samples containing the resveratrol phthalonitrile from Example 19 and 2-5 weight % of either p-BAPS, m-BAPS, or m-APB were stirred at 200° C. for 2 minutes and cured under nitrogen by heating at 200° C. for 12 h (overnight) and at 375° C. for 8 h to afford a polymer. The polymers exhibited excellent thermal and oxidative stability up to 500° C. before any weight loss was detected. Catastrophic decomposition occurred after 600° C. in air.

Example 21

Synthesis of Anethole-Derived Phthalonitrile in One Reaction Pot

To a 1000 mL, three-necked flask fitted with a thermometer and a nitrogen inlet were added 1-ethyl-2-methyl-3-(4-hydroxyphenyl)-5-hydroxyindane (10.0 g, 37.3 mmol), 4-nitrophthalonitrile (13.2 g, 76.4 mmol), powdered anhydrous $K_2CO_3$ (10.8 g, 78.3 mmol), and DMSO (200 mL). The resulting mixture was degassed with nitrogen at ambient temperature and heated at 80° C. under a nitrogen atmosphere for 8-16 h. The mixture was allowed to cool to ambient temperature and poured into a 5% aqueous HCl solution resulting in the formation of a solid. The material was broken up and collected using a Büchner funnel. The white solid was washed with 200 mL of a 5% aqueous HCl solution, and finally with 200 mL portions of water until neutral. The isolated solid was vacuum dried to yield the amorphous anethole-derived phthalonitrile (18.3 g, 95%).

Example 22

Curing of an Anethole-Derived Phthalonitrile with an Aromatic Amine

Samples containing the anethole-derived phthalonitrile from Example 21 and 2-5 weight % of either p-BAPS, m-BAPS, or m-APB were stirred at 200° C. for 2 minutes and cured under nitrogen by heating at 200° C. for 12 h (overnight) and at 350° C. for 8 h to afford a polymer. The polymers exhibited excellent thermal and oxidative stability up to 400° C. before any weight loss was detected. Catastrophic decomposition occurred after 600° C. in air.

Example 23

Synthesis of Lignin-Derived Phthalonitrile in One Reaction Pot

To a 250 ml flask fitted with a thermometer, a Dean-Stark trap with condenser, a nitrogen inlet, and a glass stopper were added 4,4'-(ethane-1,1-diyl)diphenol (8.8 g, 29.0 mmol), 4,4'-dichlorobenzophenone (3.63 g, 14.5 mmol), toluene (70 mL), and methyl sulfoxide (100 mL) and the mixture was sparged with nitrogen for 15 min. Powdered anhydrous $K_2CO_3$ (1.60 g, 11.6 mmol) and sodium hydroxide (2.08 g, 52.0 mmol) were then added, and the mixture was heated to reflux at 145-150° C. under a nitrogen atmosphere for 16 h. Over this period, water that was collected in the Dean-Stark trap was discarded. Toluene was then removed by distillation and the reaction mixture was cooled to 60° C. At this time, 4-nitrophthalonitrile (5.13 g, 29.7 mmol) was added in one portion and the reaction content was heated at 70° C. for 5 h. The mixture was allowed to cool to ambient temperature and poured into a 1% aqueous HCl solution resulting in the formation of a solid. The material was collected using a Büchner funnel and washed with water until neutral. The amorphous solid was vacuum dried to yield the phthalonitrile resin (13.7 g, 91%).

Example 24

Curing of a Lignin-Derived Phthalonitrile with an Aromatic Amine

Samples containing the lignin-derived phthalonitrile from Example 23 and 2-5 weight % of either p-BAPS, m-BAPS, or m-APB were stirred at 200° C. for 2 minutes and cured under nitrogen by heating at 200° C. for 12 h (overnight) and at 350° C. for 8 h to afford a polymer. The polymers exhibited excellent thermal and oxidative stability up to 400° C. before any weight loss was detected. Catastrophic decomposition occurred after 600° C. in air.

Example 25

Synthesis of Lignin-Derived Phthalonitrile in One Reaction Pot

To a 250 ml flask fitted with a thermometer, a Dean-Stark trap with condenser, a nitrogen inlet, and a glass stopper were added 5,5'-methylenebis(2-methoxy-4-methylphenol) (11.5 g, 39.9 mmol), 4,4'-dichlorobenzophenone (5.00 g, 14.5 mmol), toluene (70 mL), and methyl sulfoxide (100 mL) and the mixture was sparged with nitrogen for 15 min. Powdered anhydrous $K_2CO_3$ (2.20 g, 16.0 mmol) and sodium hydroxide (2.87 g, 71.8 mmol) were then added, and the mixture was heated to reflux at 145-150° C. under a nitrogen atmosphere for 16 h. Over this period, water that was collected in the Dean-Stark trap was discarded. Toluene was then removed by distillation and the reaction mixture was cooled to 60° C. At this time, 4-nitrophthalonitrile (7.07 g, 40.9 mmol) was added in one portion and the reaction content was heated at 70° C. for 5 h. The mixture was allowed to cool to ambient temperature and poured into a 1% aqueous HCl solution resulting in the formation of a solid. The material was collected using a Büchner funnel and washed with water until neutral. The amorphous solid was vacuum dried to yield the phthalonitrile resin (18.1 g, 90%).

Example 26

Curing of a Lignin-Derived Phthalonitrile with an Aromatic Amine

Samples containing the lignin-derived phthalonitrile from Example 25 and 2-5 weight % of p-BAPS, m-BAPS, or m-APB were stirred at 200° C. for 2 minutes and cured under nitrogen by heating at 200° C. for 12 h (overnight) and at 350° C. for 8 h to afford a polymer. The polymers exhibited excellent thermal and oxidative stability up to 400° C. before any weight loss was detected. Catastrophic decomposition occurred after 600° C. in air.

Example 27

Synthesis of Lignin-Derived Phthalonitrile in One Reaction Pot

To a 250 ml flask fitted with a thermometer, a Dean-Stark trap with condenser, a nitrogen inlet, and a glass stopper were added 4,4'-methylenebis(5-isopropyl-2-methylphenol) (9.50 g, 30.4 mmol), 4,4'-dichlorobenzophenone (3.82 g, 15.2 mmol), toluene (70 mL), and methyl sulfoxide (100 mL) and the mixture was sparged with nitrogen for 15 min. Powdered anhydrous $K_2CO_3$ (1.72 g, 12.5 mmol) and sodium hydroxide (2.19 g, 54.8 mmol) were then added, and the mixture was heated to reflux at 145-150° C. under a nitrogen atmosphere for 16 h. Over this period, water that was collected in the Dean-Stark trap was discarded. Toluene was then removed by distillation and the reaction mixture was cooled to 60° C. At this time, 4-nitrophthalonitrile (5.31 g, 30.7 mmol) was added in one portion and the reaction content was heated at 70° C. for 5 h. The mixture was allowed to cool to ambient temperature and poured into a 1% aqueous HCl solution resulting in the formation of a solid. The material was collected using a Büchner funnel and washed with water until neutral. The amorphous solid was vacuum dried to yield the phthalonitrile resin (14.4 g, 90%).

Example 28

Curing of a Lignin-Derived Phthalonitrile with an Aromatic Amine

Samples containing the lignin-derived phthalonitrile from Example 27 and 2-5 weight % of p-BAPS, m-BAPS, or m-APB were stirred at 200° C. for 2 minutes and cured under nitrogen by heating at 200° C. for 12 h (overnight) and at 350° C. for 8 h to afford a polymer. The polymers exhibited excellent thermal and oxidative stability up to 400° C. before any weight loss was detected. Catastrophic decomposition occurred after 600° C. in air.

Example 29

Synthesis of Lignin-Derived Phthalonitrile with 43% Excess 4,4'-methylenebis(5-isopropyl-2-methylphenol) Derived PN Resin in One Reaction Pot To a 250 ml flask fitted with a thermometer, a Dean-Stark trap with condenser, a nitrogen inlet, and a glass stopper were added 4,4'-methylenebis(5-isopropyl-2-methylphenol) (9.50 g, 30.4 mmol), 4,4'-dichlorobenzophenone (2.67 g, 10.6 mmol), toluene (70 mL), and methyl sulfoxide (100 mL) and the mixture was sparged with nitrogen for 15 min. Powdered anhydrous $K_2CO_3$ (1.72 g, 12.5 mmol) and sodium hydroxide (2.19 g, 54.8 mmol) were then added, and the mixture was heated to reflux at 145-150° C. under a nitrogen atmosphere for 16 h. Over this period, water that was collected in the Dean-Stark trap was discarded. Toluene was then removed by distillation and the reaction mixture was cooled to 60° C. At this time, 4-nitrophthalonitrile (6.87 g, 39.7 mmol) was added in one portion and the reaction content was heated at 70° C. for 5 h. The mixture was allowed to cool to ambient temperature and poured into a 1% aqueous HCl solution resulting in the formation of a solid. The material was collected using a Büchner funnel and washed with water until neutral. The amorphous solid was vacuum dried to yield the phthalonitrile resin (14.7 g, 90%).

Example 30

Curing of a Lignin-Derived Phthalonitrile with an Aromatic Amine

Samples containing the lignin-derived phthalonitrile from Example 29 and 3 weight % of either p-BAPS, m-BAPS, or m-APB were stirred at 200° C. for 2 minutes and cured under nitrogen by heating at 200° C. for 12 h (overnight) and at 350° C. for 8 h to afford a polymer. The polymers exhibited excellent thermal and oxidative stability up to 400° C. before any weight loss was detected. Catastrophic decomposition occurred after 600° C. in air.

Example 31

Synthesis of an Oligomeric Eugenol Phthalonitrile with 43% Excess 4,4'-(1,4-butane-diyl)bis-2-methoxyphenol in One Reaction Pot To a 500 mL, three-necked flask fitted with a thermometer and a nitrogen inlet were added 4,4'-(1,4-butane-diyl)bis-2-methoxyphenol (10.0 g, 33.0 mmol), 4,4'dichlorobenzophenone (2.91 g, 11.5 mmol), toluene (70 mL), and methyl sulfoxide (100 mL) and the mixture was sparged with nitrogen for 15 min. Powdered anhydrous $K_2CO_3$ (0.91 g, 6.6 mmol) and sodium hydroxide (1.19 g, 29.8 mmol) were then added, and the mixture was heated to reflux at 145-150° C. under a nitrogen atmosphere for 16 h. Over this period, water that was collected in the Dean-Stark trap was discarded. Toluene was then removed by distillation and the reaction was cooled to 60° C. At this time, 4 nitrophthalonitrile (7.45 g, 43.1 mmol) was added in one portion and the reaction was heated at 70° C. for 5 h. The mixture was allowed to cool to ambient temperature and poured into a 1% aqueous HCl solution resulting in the formation of a solid. The material was collected using a Büchner funnel and washed with water until neutral. The amorphous solid was vacuum dried to yield the phthalonitrile resin (15.7 g, 90%).

Example 32

Curing of an Oligomeric Eugenol Phthalonitrile Based on 4,4'-(1,4-butane-diyl)bis-2-methoxyphenol with an Aromatic Amine Samples containing the eugenol derived phthalonitrile from Example 31 and 2-5 weight % of either p-BAPS, m-BAPS, or m-APB were mixed by stifling at 200° C. for 2 minutes and cured by heating under nitrogen at 250° C. for 12 h (overnight) and at 350° C. for 8 h to afford a thermoset polymer. The polymers exhibited excellent thermal and oxidative stability up to 400° C. before any weight loss was detected. Catastrophic decomposition occurred after 500° C. in air.

Example 33

Synthesis of 4,4'-(1-ethyl-2-methyl-1,3-propanediyl) bisphenol Based Phthalonitrile in One Reaction Pot To a 1000 mL, three-necked flask fitted with a thermometer and a nitrogen inlet were added 4,4'-(1-ethyl-2-methyl-1,3-propanediyl)bisphenol (10.0 g, 37.0 mmol), 4-nitrophthalonitrile (12.9 g, 74.7 mmol), powdered anhydrous $K_2CO_3$ (12.8 g, 92.5 mol), and DMSO (1000 mL). The resulting mixture was degassed with nitrogen at ambient temperature and heated at 80° C. under a nitrogen atmosphere for 8-16 h. The mixture was allowed to cool to ambient temperature and poured into a 5% aqueous HCl solution resulting in the formation of a solid. The material was broken up and collected using a Büchner funnel. The white solid was washed with 200 mL of a 5% aqueous KOH solution, with 200 mL portions of distilled water until neutral, with 200 mL of a 5% aqueous HCl solution, and finally with 200 mL portions of water until neutral. The isolated solid was vacuum dried to yield the amorphous resveratrol phthalonitrile (18.4 g, 95% yield).

Example 34

Curing of a 4,4'-(1-ethyl-2-methyl-1,3-propanediyl) bisphenol Based Phthalonitrile with an Aromatic Amine Samples containing the phthalonitrile from Example 33 and 2-5 weight % of either p-BAPS, m-BAPS, or m-APB were mixed by stirring at 200° C. for 2 minutes and cured by heating under nitrogen at 250° C. for 12 h (overnight) and at 375° C. for 8 h to afford a thermoset polymer. The polymers exhibited excellent thermal and oxidative stability up to 500° C. before any weight loss was detected. Catastrophic decomposition occurred after 600° C. in air.

Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:

1. A method of making an organic salt comprising:
reacting a polyphenol with a base and optionally a dihaloaromatic compound;
wherein the polyphenol is resveratrol; dihydroresveratrol;
4,4'-(but-2-ene-1,4-diyl)bis-2-methoxyphenol;
4,4'-(1,4-butane-diyl)bis-2-methoxyphenol;
1-ethyl-2-methyl-3-(4-hydroxyphenyl)-5-hydroxyindane;
4,4'-(ethane-1,1-diyl)diphenol;
5,5'-methylenebis(2-methoxy-4-methylphenol);
4,4'-methylenebis(5-isopropyl-2-methylphenol);
4,4'-(1-ethyl-2-methyl-1,3-propanediyl)bisphenol; or
5,5'-(ethane-1,1-diyl)bis(2-methoxy-4-methylphenol);
wherein the dihaloaromatic compound if present comprises a carbonyl group, a sulfonyl group, a sulfinyl group, or a phosphoryl group; and
wherein there is a molar excess of the hydroxy groups of the polyphenol relative to halo groups of the dihaloaromatic compound if present.

2. The organic salt made by the method of claim 1.

3. The organic salt of claim 2, wherein the base is potassium carbonate or a combination of potassium carbonate and sodium hydroxide.

4. A method comprising:
reacting the organic salt of claim 2 with 4-nitrophthalonitrile to form a phthalonitrile monomer.

5. A phthalonitrile monomer made by a method comprising:
reacting a polyphenol with a base and optionally a dihaloaromatic compound to form an organic salt;
wherein the polyphenol is resveratrol; dihydroresveratrol;
4,4'-(but-2-ene-1,4-diyl)bis-2-methoxyphenol;
4,4'-(1,4-butane-diyl)bis-2-methoxyphenol;
1-ethyl-2-methyl-3-(4-hydroxyphenyl)-5-hydroxyindane;
4,4'-(ethane-1,1-diyl)diphenol;
5,5'-methylenebis(2-methoxy-4-methylphenol);
4,4'-methylenebis(5-isopropyl-2-methylphenol);
4,4'-(1-ethyl-2-methyl-1,3-propanediyl)bisphenol; or
5,5'-(ethane-1,1-diyl)bis(2-methoxy-4-methylphenol);
wherein the dihaloaromatic compound if present comprises a carbonyl group, a sulfonyl group, a sulfinyl group, or a phosphoryl group; and
wherein there is a molar excess of the hydroxy groups of the polyphenol relative to halo groups of the dihaloaromatic compound if present; and
reacting the organic salt with 4-nitrophthalonitrile to form the phthalonitrile monomer.

6. The phthalonitrile monomer of claim 5, wherein the organic salt has the formula:

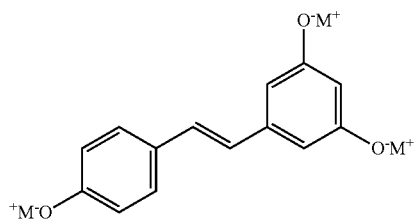

wherein each M is independently K or Na.

7. The phthalonitrile monomer of claim 5, wherein the organic salt has the formula:

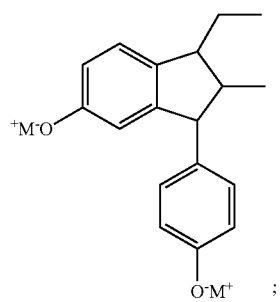

wherein each M is independently K or Na.

8. The phthalonitrile monomer of claim 5, wherein the organic salt has the formula:

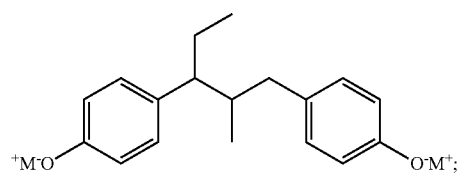

wherein each M is independently K or Na.

9. The phthalonitrile monomer of claim 5, wherein the dihaloaromatic compound is a dihalobenzophenone, 4,4'-dichlorobenzophenone, a dihalophenylsulfone, bis-4-(chlorophenyl)sulfone, a dihalophenylsulfoxide, or a dihalophenyl phosphine oxide.

10. The phthalonitrile monomer of claim 5, wherein the organic salt has the formula:

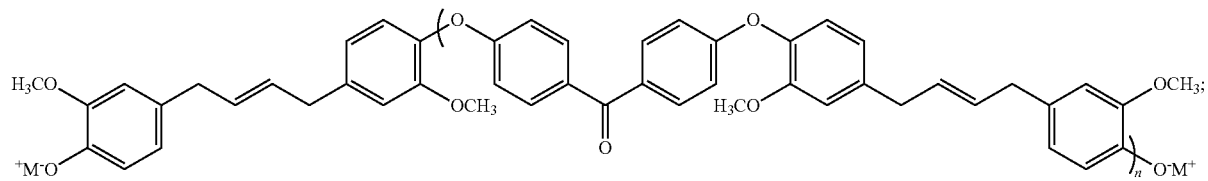

wherein n is a positive integer; and
wherein each M is independently K or Na.

11. The phthalonitrile monomer of claim 5, wherein the organic salt has the formula:

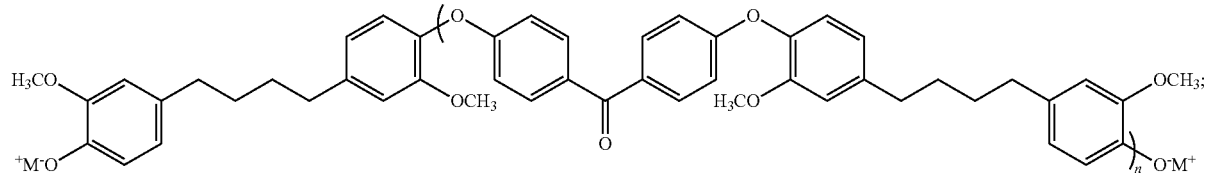

wherein n is a positive integer; and
wherein each M is independently K or Na.

12. The phthalonitrile monomer of claim 5, wherein the organic salt has the formula:

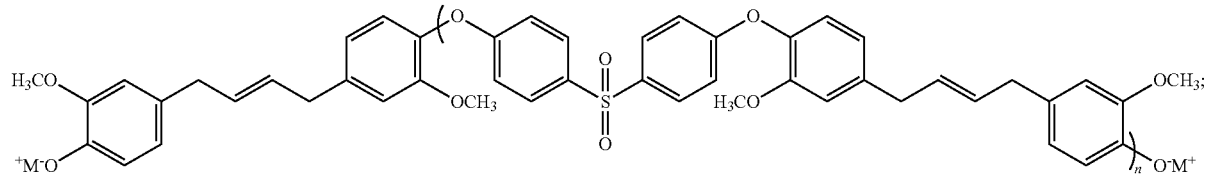

wherein n is a positive integer; and
wherein each M is independently K or Na.

13. The phthalonitrile monomer of claim 5, wherein the organic salt has the formula:

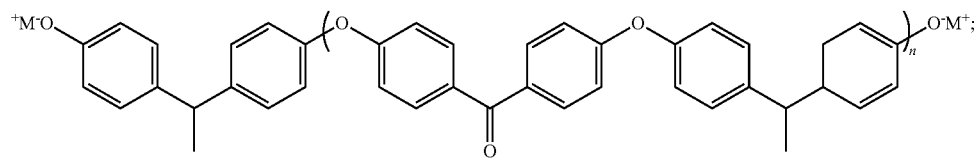

wherein n is a positive integer; and
wherein each M is independently K or Na.

14. The phthalonitrile monomer of claim 5, wherein the organic salt has the formula:

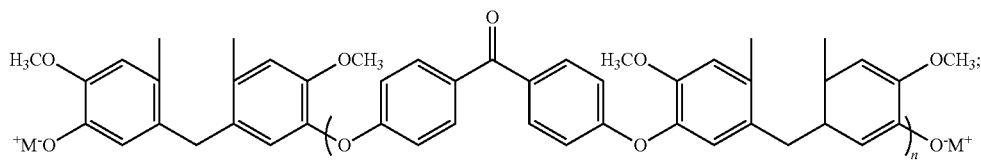

wherein n is a positive integer; and
wherein each M is independently K or Na.

15. The phthalonitrile monomer of claim 5, wherein the organic salt has the formula:

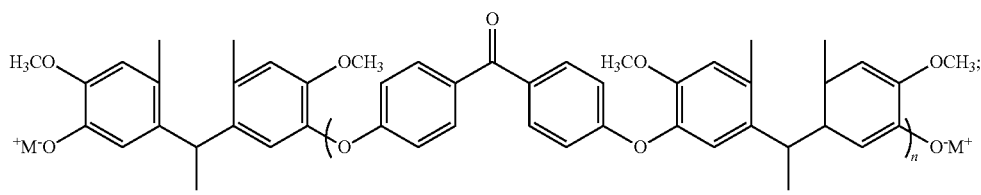

wherein n is a positive integer; and
wherein each M is independently K or Na.

16. The phthalonitrile monomer of claim 5, wherein the organic salt has the formula:

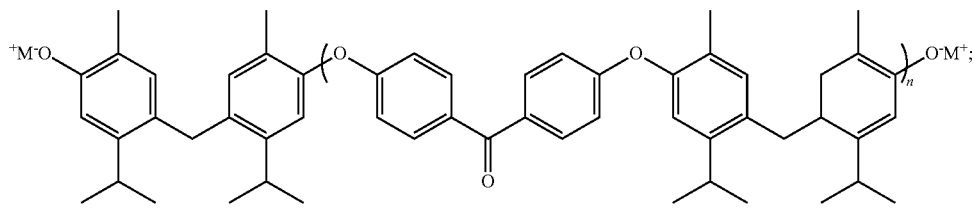

wherein n is a positive integer; and
wherein each M is independently K or Na.

17. The phthalonitrile monomer of claim 5, wherein the organic salt further comprises a salt of the polyphenol.

18. A method comprising:
curing the phthalonitrile monomer of claim 5 to form a thermoset.

19. The thermoset made by the method of claim 18.

20. A method comprising:
providing a first phthalonitrile monomer made by a method comprising:
reacting a first polyphenol with a first base and optionally a first dihaloaromatic compound to form a first organic salt;
wherein there is a molar excess of the hydroxy groups of the first polyphenol relative to halo groups of the first dihaloaromatic compound if present; and
reacting the first organic salt with 4-nitrophthalonitrile to form the first phthalonitrile monomer;
optionally, providing a second phthalonitrile monomer made by a method comprising:
reacting a second polyphenol with a second base and optionally a second dihaloaromatic compound to form a second organic salt;
wherein there is a molar excess of the hydroxy groups of the second polyphenol relative to halo groups of the second dihaloaromatic compound if present; and
reacting the second organic salt with 4-nitrophthalonitrile to form the second phthalonitrile monomer;
wherein the first polyphenol and the second polyphenol if present are independently selected from resveratrol; dihydroresveratrol;
4,4'-(but-2-ene-1,4-diyl)bis-2-methoxyphenol;
4,4'-(1,4-butane-diyl)bis-2-methoxyphenol;
1-ethyl-2-methyl-3-(4-hydroxyphenyl)-5-hydroxyindane;
4,4'-(ethane-1,1-diyl)diphenol;
5,5'-methylenebis(2-methoxy-4-methylphenol);
4,4'-methylenebis(5-isopropyl-2-methylphenol);
4,4'-(1-ethyl-2-methyl-1,3-propanediyl)bisphenol; or
5,5'-(ethane-1,1-diyl)bis(2-methoxy-4-methylphenol);
wherein the first dihaloaromatic compound if present and the second dihaloaromatic compound if present each comprise a group independently selected from a carbonyl group, a sulfonyl group, a sulfinyl group, or a phosphoryl group;
wherein the first base and the second base if present are the same or different;

wherein the first phthalonitrile monomer and the second phthalonitrile monomer if present are different; and making a phthalonitrile mixture by mixing the first phthalonitrile monomer with one or more of: the second phthalonitrile monomer if present; a monophthalonitrile compound; 1,3,5-tris(3,4-dicyanophenoxy)benzene;

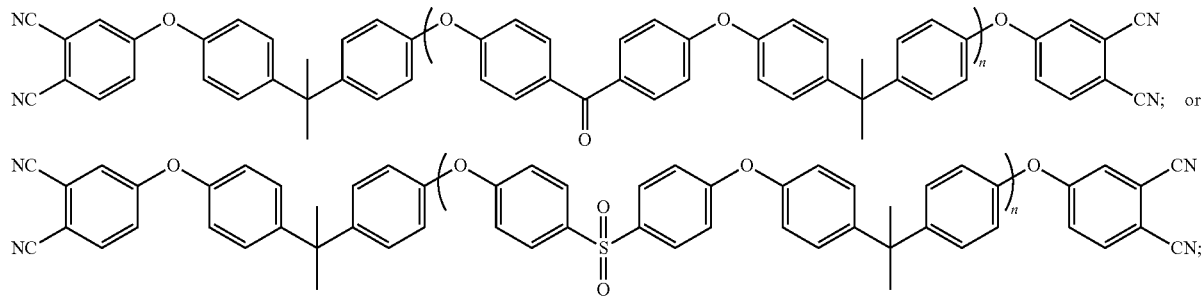

wherein n is a positive integer; and
curing the phthalonitrile mixture to form a thermoset.
21. The thermoset made by the method of claim 20.
22. A method comprising:
making a phthalonitrile mixture by mixing 1,3,5-tris(3,4-dicyanophenoxy)benzene with

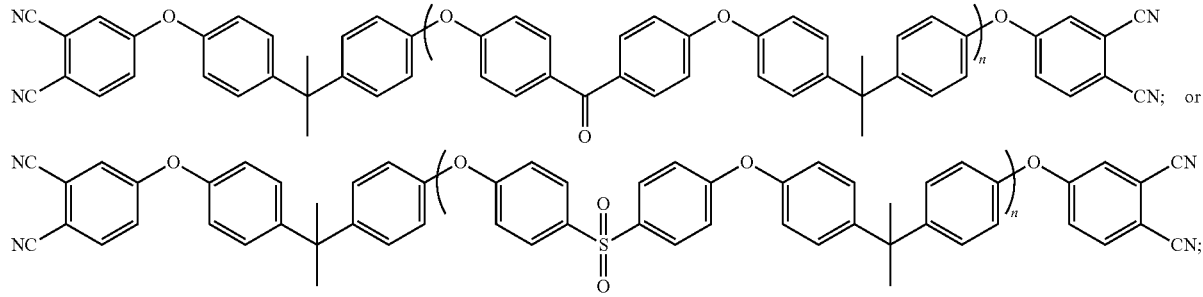

wherein n is a positive integer; and
curing the phthalonitrile mixture to form a thermoset.
23. The thermoset made by the method of claim 22.
24. The phthalonitrile monomer of claim 5, wherein the organic salt has the formula:

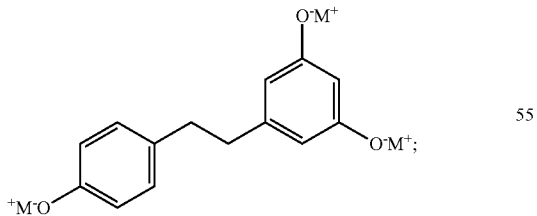

wherein each M is independently K or Na.

* * * * *